(12) United States Patent
Kumakhov

(10) Patent No.: US 6,996,207 B2
(45) Date of Patent: Feb. 7, 2006

(54) X-RAY MICROSCOPE

(76) Inventor: Muradin Abubekirovich Kumakhov, ul. Narodnogo Opolcheniya, d. 38, kv. 55, Moscow 123298 (RU)

( * ) Notice: Subject to any disclaimer, the term of this patent is extended or adjusted under 35 U.S.C. 154(b) by 101 days.

(21) Appl. No.: 10/276,154

(22) PCT Filed: Mar. 5, 2002

(86) PCT No.: PCT/RU02/00075

§ 371 (c)(1),
(2), (4) Date: Nov. 13, 2002

(87) PCT Pub. No.: WO03/075286

PCT Pub. Date: Sep. 12, 2003

(65) Prior Publication Data

US 2004/0062347 A1  Apr. 1, 2004

(51) Int. Cl.
*G21K 7/00* (2006.01)
(52) U.S. Cl. .......................... 378/43; 378/84
(58) Field of Classification Search .................. 378/43, 378/84, 145, 147, 149; 250/370.08, 370.09, 250/505.1
See application file for complete search history.

(56) References Cited

U.S. PATENT DOCUMENTS

| | | | | |
|---|---|---|---|---|
| 5,045,696 A | * | 9/1991 | Hirose | 250/306 |
| 5,497,008 A | * | 3/1996 | Kumakhov | 250/505.1 |
| 6,271,534 B1 | * | 8/2001 | Kumakhov | 250/505.1 |

FOREIGN PATENT DOCUMENTS

WO  WO 96/01991  1/1996
WO  WO 00/73772 A1 * 12/2000

OTHER PUBLICATIONS

Encyclopedia "Electronica," Moscow, "Sovetskaya Entsiklopediya" publishing house, 1991, p. 478.
Physical Encyclopedia, Moscow, "Sovetskaya Entsiklopediya" publishing house, 1984, p. 639.

* cited by examiner

*Primary Examiner*—David V. Bruce
*Assistant Examiner*—Courtney Thomas
(74) *Attorney, Agent, or Firm*—William H. Holt

(57) ABSTRACT

X-ray microscope comprise extended X-ray source, as well as means for placement of test object 3 and recording means, and located between them X-ray capillary lens. Channels of the latter are diverging towards recording means. Means for placement of the test object is located between extended X-ray source and lesser end side of the X-ray capillary lens. The device is characterized in that the walls of the channels (14, 16) for radiation transmission have a coating or are made of material absorbing or scattering X-ray radiation, and have lateral surface shape of truncated cone or pyramid, or that of cylinder or prism. With specified choice of the material, phenomenon of total external reflection is excluded, while rectilinearity of longitudinal axes of the channels ensures their functioning as collimators. Therefore, channels capture radiation only from the fragments of the test object 3 situated exactly opposite their entrances. As compared with known device, possibility is excluded of radiation capture entering channel 18 at angles from zero to critical angle $\theta_c$ of total external reflection. Due to this, resolution is fully determined by technological possibilities of decreasing dimension of the channel entrance. The ability of using extended X-ray source allows to reduce substantially time of exposure with simultaneous decrease in the X-ray tube power.

10 Claims, 6 Drawing Sheets

X-RAY MICROSCOPE

FIELD OF THE INVENTION

The invention relates to projection microscopy utilizing radiation methods, in particular, to means of obtaining enlarged shadow projection of an object, including its internal structure, by use of X-ray radiation.

BACKGROUND OF THE INVENTION

X-ray microscope is known, which allows to obtain image of internal structure of objects. The operation of such microscope is based on principle of shadow projection of the object in divergent X-ray beam emitted by a point source (Encyclopedia "Electronica", Moscow, "Sovetskaya Entsiklopediya" publishing house, 1991, p.478) [1]. This microscope has been called shadow, or projection, microscope. The projection microscope comprise usually a microfocus X-ray tube, a chamber for placement of the studied object, and recording means. Resolution of projection X-ray microscope is the greater, the smaller size of radiation source and its distance from the object. The utilization is known, in particular, in such microscopes of the tubes with focal spot of 0.1 to 1 $\mu$m in diameter [1]. To further reduce the effective size of the source, diaphragming is used (Physical Encyclopedia, Moscow, "Sovetskaya Entsiklopediya" publishing house, 1984, p.639) [2].

However, with decreasing source size or with its diaphragming, its intensity becomes insufficient to ensure acceptable contrast ratio of the enlarged image. Overcoming of this drawback requires substantial increase in exposure time. Increase of the source size for enhancement of its effective intensity results in blurring of the image obtained and decrease in resolution.

With creation of X-ray capillary optics of total external reflection, the possibility has arisen of utilization in X-ray microscopes of extended (comparable to the object studied) X-ray sources. In such microscopes, chamber with the object studied is placed between extended X-ray source and entrance end face of X-ray lens with channels diverging towards image recording means (international application PCT/RU 94/00189, international publication WO 96/01991, 25.01.96 [3]). Specifically, said reference discloses use of conical X-ray lenses and bell-type lenses, the latter ones being noted as more efficient. Increase in the source size has no effect on resolution of these microscopes, since it corresponds to the size of the object's fragment brought into field of vision of separate channel of X-ray capillary lens. The X-ray microscope of said design is the most close to the one proposed.

However, with decrease in diameter of the separate channels down to the level reached in the state-of-the-art technologies in monolithic and, in particular, in integral lenses (U.S. Pat. No. 6,271,534, publ. 07.08.2001 [4]), entrance size of the separate channel in X-ray lens ceases to be a determining factor. This is accounted for by the fact of size $\Delta$ of the field of vision of lens' separate channel mentioned being of the order $$\Delta = d + 2L\theta_c, \quad (1)$$

where d denotes entrance diameter of separate channel,
 L is a distance between the object studied and entrance of the X-ray lens channel, and
 $\theta_c$ is critical angle of total external reflection of the channels walls material.

With small diameters d and low radiation energies used, in particular, in studies of biological objects, when angle $\theta_c$ may reach $10^{-2}$ radian, second term in the expression (1) above becomes dominant. Thus, for example, for L=1 mm and d=0,1 micron we obtain:

$$d=0,1 \quad \text{micron}=10^{-7} \quad m<<2\cdot 10^{-5} \quad m=2\cdot 1\cdot 10^{-3}$$
$$m\cdot 10^{-2}=2L\theta_c.$$

Consequently, developments in manufacturing technology of X-ray lenses don't allow to enhance precision characteristics of X-ray microscopes of known design utilizing extended sources.

DISCLOSURE OF INVENTION

The invention proposed is aimed at producing a technical result consisting in resolution increase of the projection microscope using X-ray radiation by decreasing channels diameter of the capillary lens used while maintaining possibility of utilizing extended (including that with size exceeding the object studied) source with simultaneous elimination of resolution dependence on the energy of radiation used. The types of the technical result mentioned are combined with a small exposure time.

To achieve this technical result, the X-ray microscope proposed, similar to the most close one known from patent [3], comprise extended X-ray source, as well as means for placement of the object studied and recording means, with X-ray capillary lens placed between them, having channels for radiation transmission diverging towards recording means. At that, means for placement of the object studied is situated between the extended X-ray source and entrance (smaller) end face of the X-ray capillary lens.

Unlike the most close known device, in the X-ray microscope proposed walls of the X-ray capillary lens channels have internal coating, or are made of material, absorbing or scattering X-ray radiation, and are shaped as lateral surface of truncated cone or pyramid, or that of cylinder or prism.

With the first two named types of surface shape of the radiation transmission channels' walls their cross section increases uniformly from entrance to exit, while with two latters it remains constant over the channel length. It is essential that in all these cases optical axes of the channels are rectilinear. Making of the walls of radiation transmission channels from the material absorbing or scattering X-ray radiation, or their coating from inside with such a material provides for the absence of radiation reflection during its passage through the channels. In consequence of this, the channels function by the principle of collimators, and trapping by them of the radiation which in further propagation would encounter the wall becomes impossible. As a result, each channel may entrap just that radiation which comes through the fragment of the object studied situated exactly opposite entrance of this channel. Therefore, size of the viewing field for a separate channel is determined by formula (1) without second term on the right-hand side.

BRIEF DESCRIPTION OF THE DRAWINGS

The invention proposed is illustrated with drawings, in which.

EMBODIMENTS OF THE INVENTION

Figure 1:
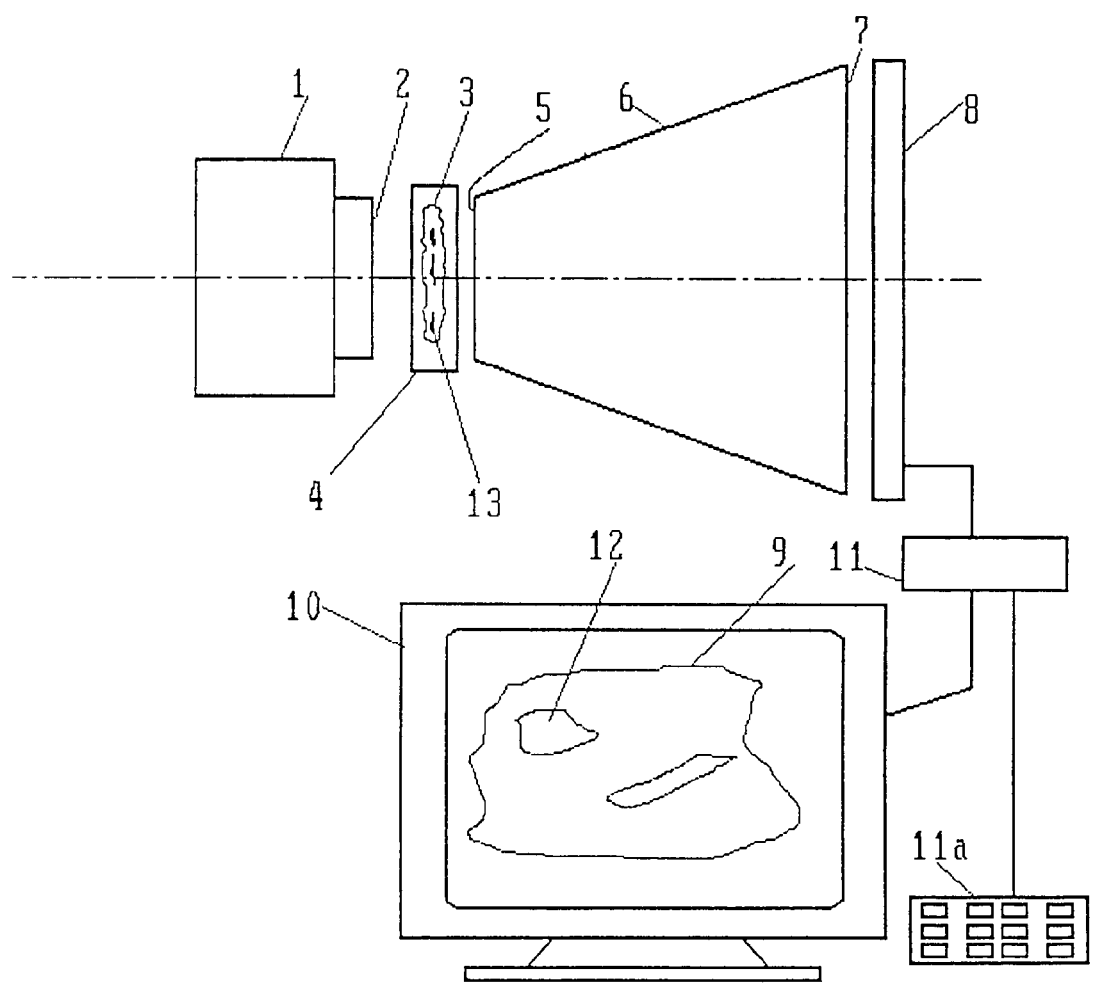
FIG. 1 shows general layout diagram of X-ray microscope.

The X-ray microscope proposed comprises (FIG. 1) X-ray source 1 having extended aperture 2 with size not less than that of the test object 3. The latter is situated in the means (chamber 4) for placement of the test object. Located in maximum proximity from this means is an entrance (smaller) end side 5 of X-ray capillary lens 6. Located near exit (larger) end side 7 is sensitive to X-ray radiation recording means 8. An image 9 of density distribution of X-ray radiation passing through the test object 3 and transmitted with lens 6 from its entrance 5 to exit 7 end side, recorded with this means, is displayed on monitor 10. At that, enlargement of linear dimensions of image of the object 3 takes place in proportion to linear dimensions ratio of exit 7 and entrance 5 end sides of the lens 6.

Preliminarily, output signals of recording means 8 may be subjected to processing in personal computer or in special-purpose computing means 11 equipped with control unit 11a. Thus, for example, means 11 may register an image in the absence of test object 3, which depicts non-uniformity of radiation intensity in aperture 2 and non-uniformity of its losses on passage through walls of chamber 4 and lens 6, as well as irregularity of detecting elements sensitivity over area of means 8 for image 9 recording. Later on, during observation of the test object, this recorded picture may be used to correct the image obtained so that it will reflect only intrinsic non-uniformity of the test object density. Due to this, image 9 on the monitor 10 screen presents true pattern 12 of non-uniformities 13 of internal structure of the object 3.

In fact, function of the lens 6 lies in splitting of shadow image of the object 3 at the entrance end side of lens 6 into elements by the number of lens channels and in transmission of each of such elements (as corresponding intensity of X-ray radiation passing through one or another fragment of the object 3) to corresponding detecting element of recording means 8. The resolution equal to entrance diameter of the lens channels may be realized if output signals of each one of the lens channels may be recorded separately, without "mixing" with output signals from other channels. Therefore, the abovementioned enlargement ratio should correspond to the size of resolution element (separate detecting element) of the recording means 8.

The provision of such correspondence not necessarily requires actual enlargement of the image element at the lens 7 output in comparison with entrance size. It is sufficient to realize said possibility of separate reception of signals corresponding to each of the image elements. This condition may be met in any of the lens designs shown in FIG. 2 and FIG. 3.

Figure 2:
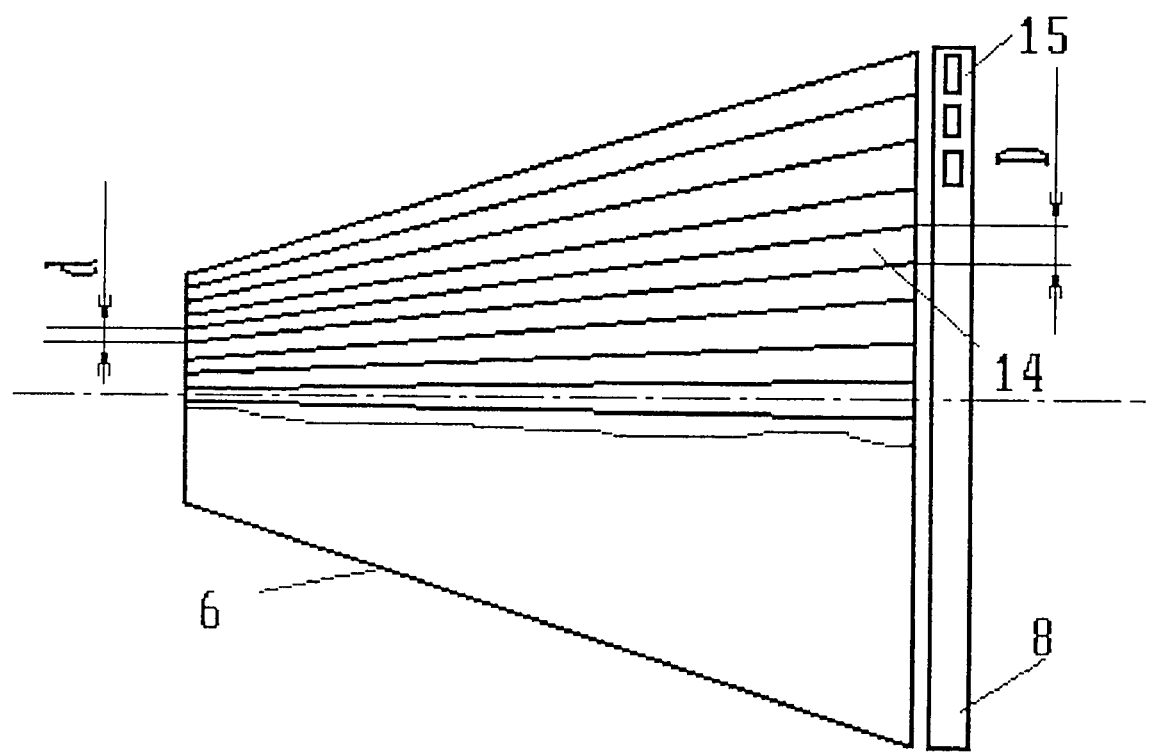
FIG. 2 shows design of a lens belonging to X-ray microscope with divergent channels of radiation transmission having cross section increasing towards exit side.
Figure 3:
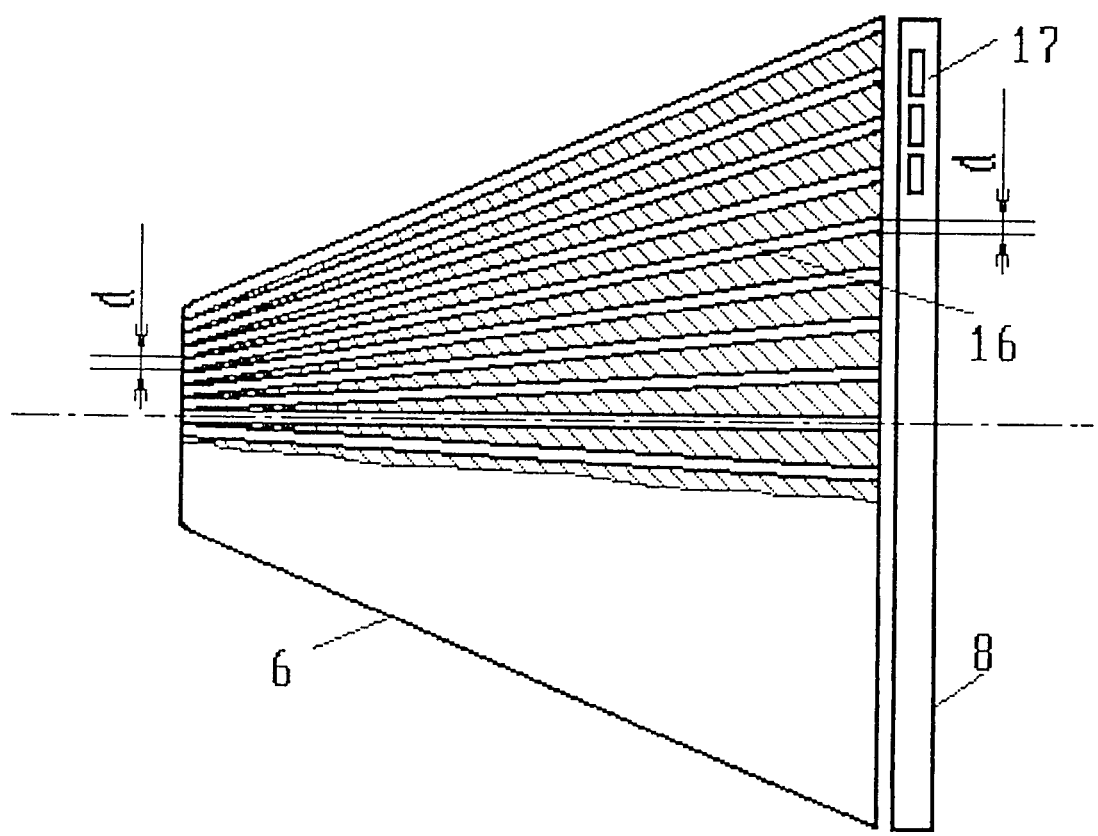
FIG. 3 shows design of a lens belonging to X-ray microscope with divergent channels of radiation transmission having constant cross section over the length.
Figure 4:
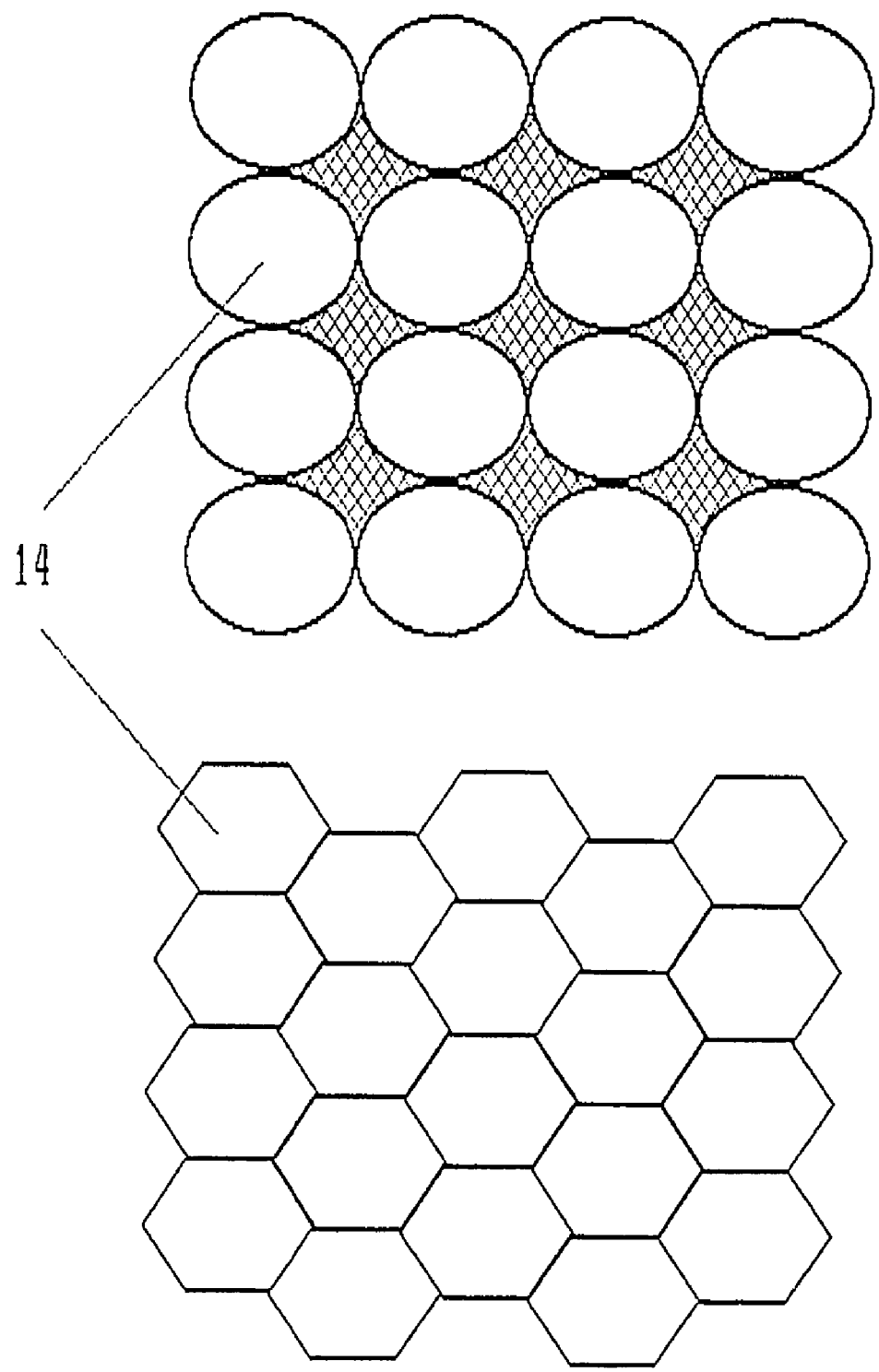
FIG. 4 shows cross-sectional view of a lens in the case corresponding to FIG. 2, with two wall shapes of the radiation transmission channel.
Figure 5:
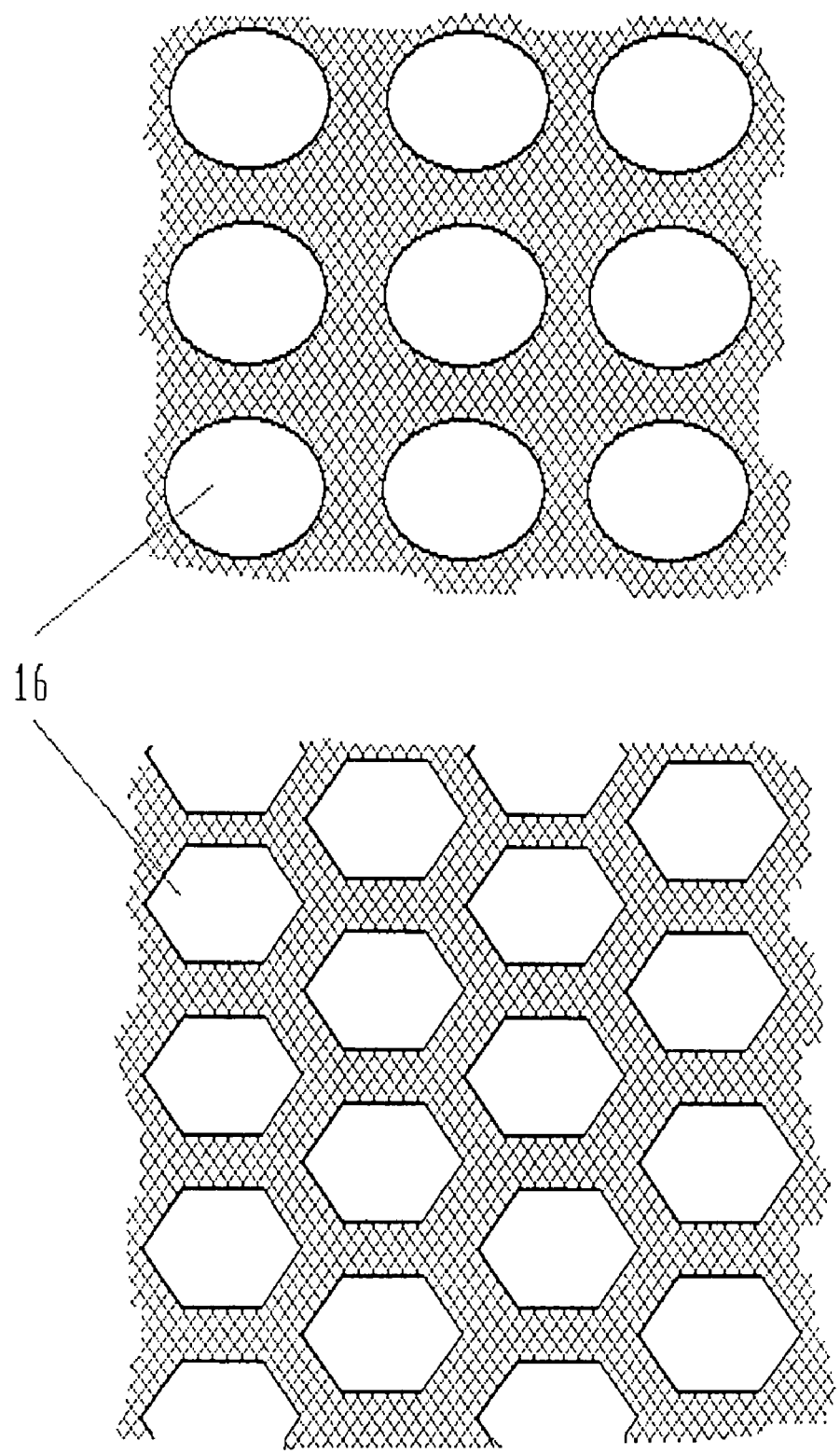
FIG. 5 shows cross-sectional view of a lens in the case corresponding to FIG. 3, with two wall shapes of the radiation transmission channel.

In the first one of them (FIG. 2) channels 14 occupy practically all lens volume, their cross sections changing with length under the same law as cross section of the lens as a whole. Channels in the lens design of FIG. 2 may have a shape, in particular, of circular cone or hexahedral pyramid. Their cross section is shown in FIG. 4. Such shape is the most feasible technologically. Ratio of exit D and entrance d diameters (for circular shape of cross section) determines said degree of enlargement. To realize potentially possible resolution, sensitive detecting elements of the means 8 should not exceed D in size, while being positioned opposite outlets of the lens channels. FIG. 2 shows several of such elements 15. The same condition should be met in case of the lens shown in FIG. 3 with cross section of channels 16 being constant over the length and their exit diameter being equal to entrance diameter d. Several of the detecting elements 17 complying with this condition are also shown in FIG. 3. The most technologically feasible shapes of the channels in lens design according to FIG. 3 are circular cylinder and hexahedral prism. Their cross section is shown in FIG. 5.

Spaces between channels of radiation transmission should be non-transparent for X-ray radiation (otherwise, they also should be considered to be "channels").

The design of FIG. 2 is somewhat more advantageous energy-wise. While receiving radiation from fragment of the object of the same size as that in design of FIG. 3 and providing for about the same resolution, it allows to capture greater part of this fragment's radiation due to divergent nature of the channels.

Figure 6:
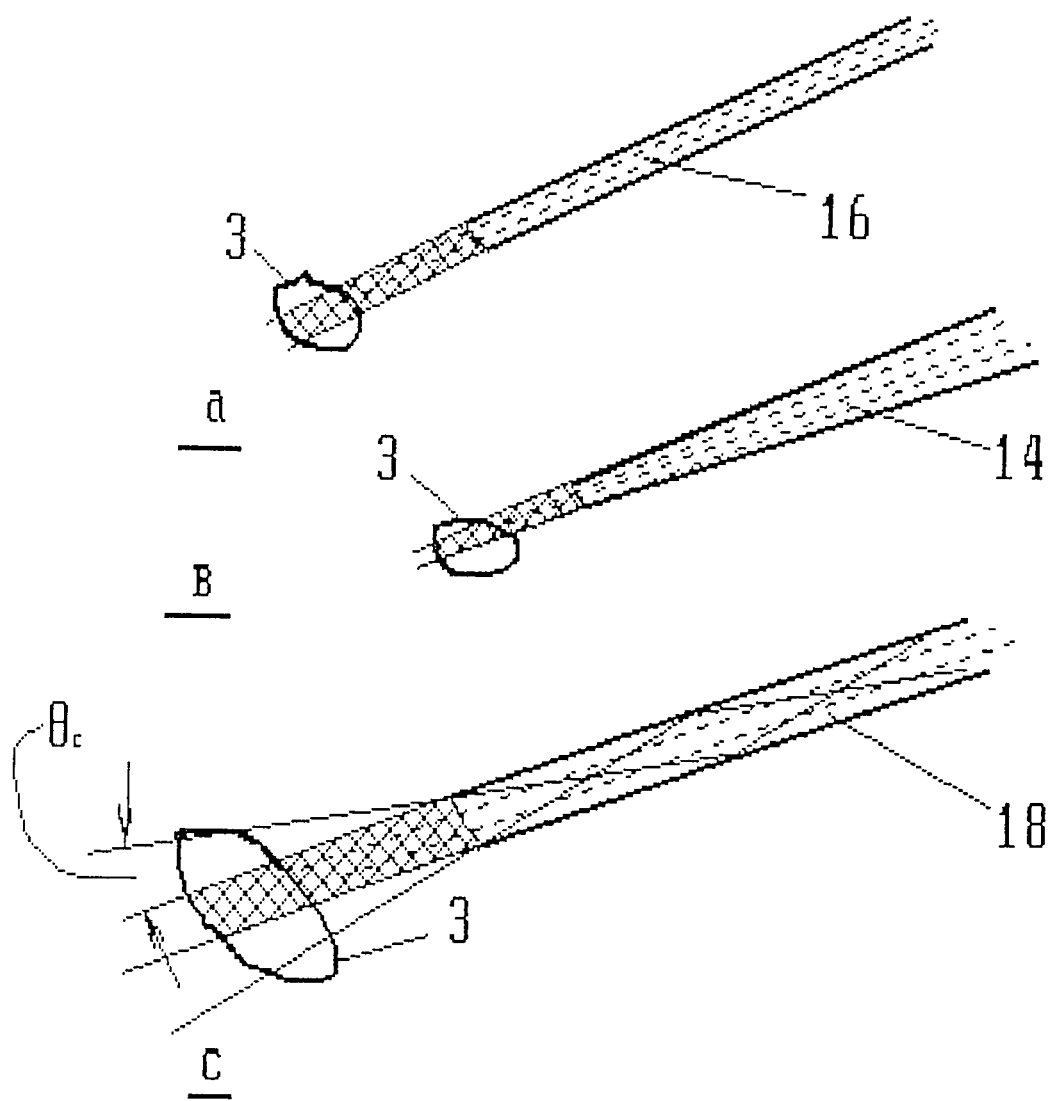
FIG. 6 shows fields of vision of separate lens channels and propagation paths of X-ray radiation quanta in the channels of proposed and known devices.

In both designs, radiation may be captured only from the points of object fragments located strictly in zones limited with continuations of the channels (see FIG. 6a and FIG. 6b). Due to suggested choice of the channel walls materials or materials for their coating, radiation entering the channel at an angle to its wall is absorbed or scattered and is not transmitted to the exit. In FIGS. 6a and 6b dotted lines show propagation paths of X-ray radiation quanta passing through to the channel's exit, which may be only the rectilinear ones. On the contrary, in known device [3] utilizing principle of total external reflection, radiation may be transmitted through the channels 18 which comes to the channels entrance from the object's fragments located outside of zones shown in FIG. 6a and FIG. 6b (see FIG. 6c). This may take place if direction of radiation propagation at the entrance to the channel forms with its walls an angle smaller than the critical $\theta_c$. Therefore, as is shown in FIG. 6c, quanta coming to the channel exit are propagating both by rectilinear (indicated with dotted lines) and broken-line (indicated with solid lines) paths.

In the experiments staged, object image has been obtained with resolution of 1 micron order for source having linear dimensions about 0.1 mm, i.e. area of the source aperture exceeded the resolution element by about 10,000-fold. There exist all the prerequisites necessary to obtain in future resolution on the level of 0.1 micron and better.

The essential factor determining prospects of practical use of microscope proposed is the rate of information gaining. According to estimates performed, it may be higher by a factor of (10–100) thousand than that with utilization of usual projection X-ray microscopy method.

Such an advantage is attained due to restriction removal on the intensity of the source used. Since it should not be a microfocus one and may have finite dimensions, highly efficient intensity is attainable even with low power of X-ray tube.

The above examples relate to the tube having power below 10 W and conical X-ray lens with channels number of the order of $10^6$.

INDUSTRIAL APPLICABILITY

The device proposed may be realized in practice in any one of the numerous embodiments described, allowing for a choice of both lens design and specific shape of the channels depending on manufacturing facilities and other grounds for one or another preferences.

The experimentally confirmed characteristics allow to expect for wide use of the X-ray microscope proposed both in directly industry, in particular, in microtechnologies, and in scientific research, first of all in biology and medicine.

All of the above concerning design principles and the result achieved is equally applicable to microscopes utilizing other kinds of radiation in the form of neutral particles flux, in particular, neutrons, gamma quanta, ultraviolet and infrared radiation, visible light, as well as radiation in the form charged particles flux, for example, ions.

INFORMATION SOURCES

1. Encyclopedia "Electronica", Moscow, "Sovetskaya Entsiklopediya" publishing house, 1991.
2. Physical Encyclopedia, Moscow, "Sovetskaya Entsiklopediya" publishing house, 1984.
3. International application PCT/RU 94/00189, international publication WO 96/01991, 25.01.96.
4. U.S. Pat. No. 6,271,534, publ. 07.08.2001.

What is claimed is:

1. An X-ray microscope comprising an extended X-ray source, means for placement of a test object, recording means for recording a shadow image of said test object, and an X-ray capillary lens having channels for radiation transmission diverging towards said recording means; said means for placement of the test object being installed between the extended X-ray source and a lesser end side of the X-ray capillary lens, characterized in that the channels for radiation transmission are comprised of walls, and said walls have a coating of material for scattering X-ray radiation for excluding total external reflection.

2. The X-ray microscope according to claim 1, characterized in that the channels for radiation transmission have constant cross section through their length.

3. The X-ray microscope according to claim 2, characterized in that the channels for radiation transmission have a lateral surface shaped as a prism or cylinder.

4. The X-ray microscope according to claim 1, characterized in that the channels for radiation transmission have a cross section increasing uniformly in the direction from their inlet to their outlet.

5. The X-ray microscope according to claim 4, characterized in that the channels for radiation transmission have a lateral surface shaped as a truncated cone or pyramid.

6. An X-ray microscope comprising an extended X-ray source, means for placement of a test object, recording means for recording a shadow image of said test object, and an X-ray capillary lens having channels for radiation transmission diverging towards said recording means; said means for placement of the test object being installed between the extended X-ray source and a lesser end side of the X-ray capillary lens, characterized in that the channels for radiation transmission include walls formed of material for scattering X-ray radiation for excluding total external reflection.

7. The X-ray microscope according to claim 6, characterized in that the channels for radiation transmission have constant cross section through out their length.

8. The X-ray microscope according to claim 7, characterized in that the channels for radiation transmission have a lateral surface shaped as a prism or cylinder.

9. The X-ray microscope according to claim 6, characterized in that the channels for radiation transmission have a cross section increasing uniformly in the direction from their inlet to their outlet.

10. The X-ray microscope according to claim 9, characterized in that the channels for radiation transmission have a lateral surface shaped as a truncated cone or pyramid.

* * * * *